(12) United States Patent
Rasmussen et al.

(10) Patent No.: US 7,686,790 B2
(45) Date of Patent: Mar. 30, 2010

(54) NONLINEAR, UNDULATING PERIMETER EMBOSSING IN AN ABSORBENT ARTICLE

(75) Inventors: Shelley R. Rasmussen, Oshkosh, WI (US); Marcus D. Weiher, Appleton, WI (US); Teresa M. Zander, Bonduel, WI (US); Laura J. Walker, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 339 days.

(21) Appl. No.: 10/379,942

(22) Filed: Mar. 4, 2003

(65) Prior Publication Data

US 2004/0176734 A1 Sep. 9, 2004

(51) Int. Cl.
*A61F 13/15* (2006.01)
*A61F 13/20* (2006.01)

(52) U.S. Cl. .................. 604/317; 604/379; 604/380; 604/385.01; 604/385.03; 604/385.04; 604/382; 604/378; 604/367; 604/358

(58) Field of Classification Search .................. 604/317, 604/358, 383, 385.01, 385.101, 385.23, 380, 604/379, 365, 367, 378, 382, 384, 385.03, 604/385.04; 128/121.1; 428/103; D24/124–126; D5/20, 25, 35
See application file for complete search history.

(56) References Cited

U.S. PATENT DOCUMENTS

| | | | |
|---|---|---|---|
| 1,357,141 A | | 10/1920 | Bibb |
| 2,788,003 A | * | 4/1957 | Morin .......................... 604/366 |
| 3,494,362 A | * | 2/1970 | Burgeni ....................... 604/374 |
| 3,874,836 A | | 4/1975 | Johnson et al. |
| 3,881,490 A | * | 5/1975 | Whitehead et al. ........... 604/366 |
| 4,159,677 A | * | 7/1979 | Smith ........................... 101/23 |
| 4,289,725 A | | 9/1981 | Muller et al. |
| 4,624,666 A | * | 11/1986 | DeRossett et al. ............ 604/366 |
| 4,758,240 A | * | 7/1988 | Glassman ..................... 604/379 |
| 4,781,710 A | * | 11/1988 | Megison et al. .............. 604/378 |
| 4,844,965 A | * | 7/1989 | Foxman ........................ 428/91 |
| 5,173,313 A | | 12/1992 | Sato et al. |
| 5,211,641 A | | 5/1993 | Roos et al. |
| D336,515 S | * | 6/1993 | Voelker-Ferrier et al. .. D24/125 |
| D350,200 S | * | 8/1994 | Gerhartl ..................... D24/125 |
| 5,429,630 A | * | 7/1995 | Beal et al. ............... 604/385.04 |
| 5,451,442 A | * | 9/1995 | Pieniak et al. ................. 428/54 |
| 5,514,104 A | * | 5/1996 | Cole et al. ................... 604/366 |
| D392,736 S | * | 3/1998 | Erickson ..................... D24/125 |
| 5,807,365 A | * | 9/1998 | Luceri ......................... 604/367 |

(Continued)

FOREIGN PATENT DOCUMENTS

EP 1 321 286 A1 6/2003

(Continued)

*Primary Examiner*—Tatyana Zalukaeva
*Assistant Examiner*—Ginger T Chapman
(74) *Attorney, Agent, or Firm*—Bryan R. Rosiejka; David J. Arteman

(57) ABSTRACT

An absorbent feminine care article (20) having a longitudinal direction (22), a lateral direction (24), first and second longitudinally opposed end portions (72, 72a), and an intermediate portion (76) located between the end portions. The article (20) comprises an absorbent body structure (30) sandwiched between a cover (26) and a baffle (28). In a particular aspect, the absorbent structure (30) can include one or more distinctively configured embossment regions (34), and the embossment regions can be distributed along the intermediate portion (76) of the article.

15 Claims, 10 Drawing Sheets

U.S. PATENT DOCUMENTS

| | | | |
|---|---|---|---|
| 5,858,515 A | 1/1999 | Stokes et al. | |
| 5,891,118 A * | 4/1999 | Toyoshima et al. | 604/366 |
| D411,006 S * | 6/1999 | Nixon et al. | D24/125 |
| 5,925,026 A * | 7/1999 | Arteman et al. | 604/383 |
| 5,941,863 A * | 8/1999 | Guidotti et al. | 604/378 |
| D426,889 S * | 6/2000 | Bissah et al. | D24/125 |
| 6,170,393 B1 | 1/2001 | Hook et al. | |
| D439,057 S * | 3/2001 | Bissah et al. | D5/35 |
| 6,251,207 B1 * | 6/2001 | Schultz et al. | 156/209 |
| 6,326,525 B1 * | 12/2001 | Hamajima et al. | 604/378 |
| 6,380,455 B1 * | 4/2002 | Moder et al. | 604/358 |
| 6,506,961 B1 * | 1/2003 | Levy | 604/380 |
| 6,525,239 B2 * | 2/2003 | Cole | 604/382 |
| 6,630,054 B1 * | 10/2003 | Graef et al. | 162/101 |
| 7,048,885 B2 * | 5/2006 | Weiher et al. | 264/284 |
| 2001/0007065 A1 * | 7/2001 | Blanchard et al. | 604/369 |
| 2002/0017354 A1 * | 2/2002 | Riddell | 156/62.4 |
| 2002/0197346 A1 | 12/2002 | Papadopoulos | |
| 2003/0187416 A1 * | 10/2003 | Shimoe et al. | 604/379 |
| 2005/0035492 A1 * | 2/2005 | Weiher et al. | 264/284 |
| 2005/0064058 A1 * | 3/2005 | Lake et al. | 425/194 |

FOREIGN PATENT DOCUMENTS

| | | |
|---|---|---|
| GB | 2 370 780 A | 7/2002 |
| WO | WO 90/05514 A1 | 5/1990 |
| WO | WO 95/07674 A | 3/1995 |
| WO | WO 97/20107 A1 | 6/1997 |
| WO | WO 97/48551 A1 | 12/1997 |
| WO | WO 98/51250 A | 11/1998 |

* cited by examiner

NONLINEAR, UNDULATING PERIMETER EMBOSSING IN AN ABSORBENT ARTICLE

FIELD OF THE INVENTION

The present invention relates to an absorbent article. More particularly, the present invention pertains to an absorbent system for a feminine care article, such as an absorbent feminine care pad.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that, feminine care articles have been employed to absorb and hold liquids, such as urine and/or menses. The absorbent articles have included various systems of liquid-handling layers, such as intake layers, distribution layers, retention layers and the like. Additionally, the absorbent articles have included patterns of embossments distributed on the bodyside surface of the article to provide a hinging action, or to inhibit or direct a desired flow of liquids. Other arrangements of the absorbent articles have included wing portions which can help to hold the article in place at a selected location in a wearer's undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent systems, however, have not provided desired combinations of comfort, rapid intake of liquid, low surface staining, low leakage and surface dryness. When such conventional absorbent systems have been constructed to include embossments, the embossments have not been sufficiently effective during ordinary use, and the liquid-handling properties of the article have been less than desired. As a result, there has been a continued need for improved embossed absorbent systems that provide more secure levels of liquid intake and storage, along with increased levels of confidence to the wearer.

BRIEF DESCRIPTION OF THE INVENTION

Generally stated, the present invention provides an absorbent article having a longitudinal direction, a lateral direction, first and second longitudinally opposed end portions, and an intermediate portion located between the end portions. The article comprises an absorbent body sandwiched between a cover and a baffle. In a particular aspect, the article can include a distinctive configuration of embossments which can better provide a controlled deformation of the article and maintain a desired shape. The article can also more effectively provide open channel regions for inhibiting, directing, or otherwise controlling a desired flow of liquids. In other aspects, the article can include nonlinear embossments which extend generally longitudinally in the intermediate portion of the article and are located generally proximate the lateral side edges of the article. In further aspects, the embossments can be curvilinear, or can have an undulating, serpentine pattern-shape. Still other aspects can include parameters that help to operatively maintain a more effective condition of the embossments.

By incorporating its various features and configurations, the article of the invention can, for example, provide an improved pattern of embossments that can better maintain their shape, and can better retain a desired open-channel configuration during ordinary use. The article can provide an improved direction and regulation of liquid flow. Additionally, the article can provide a controlled deformation, and can be resistant to undesired bunching and twisting. The article can be less susceptible to premature leakage, and can provide greater protection and confidence to the wearer. Particular features can provide improved aesthetics and visual cues or indicators of absorbency and leakage protection.

BRIEF DESCRIPTION OF THE DRAWINGS

The various features, aspects and advantages of the present invention will become better understood with reference to the following description, appended claims and accompanying drawings where:

DETAILED DESCRIPTION OF THE INVENTION

Figure 1:
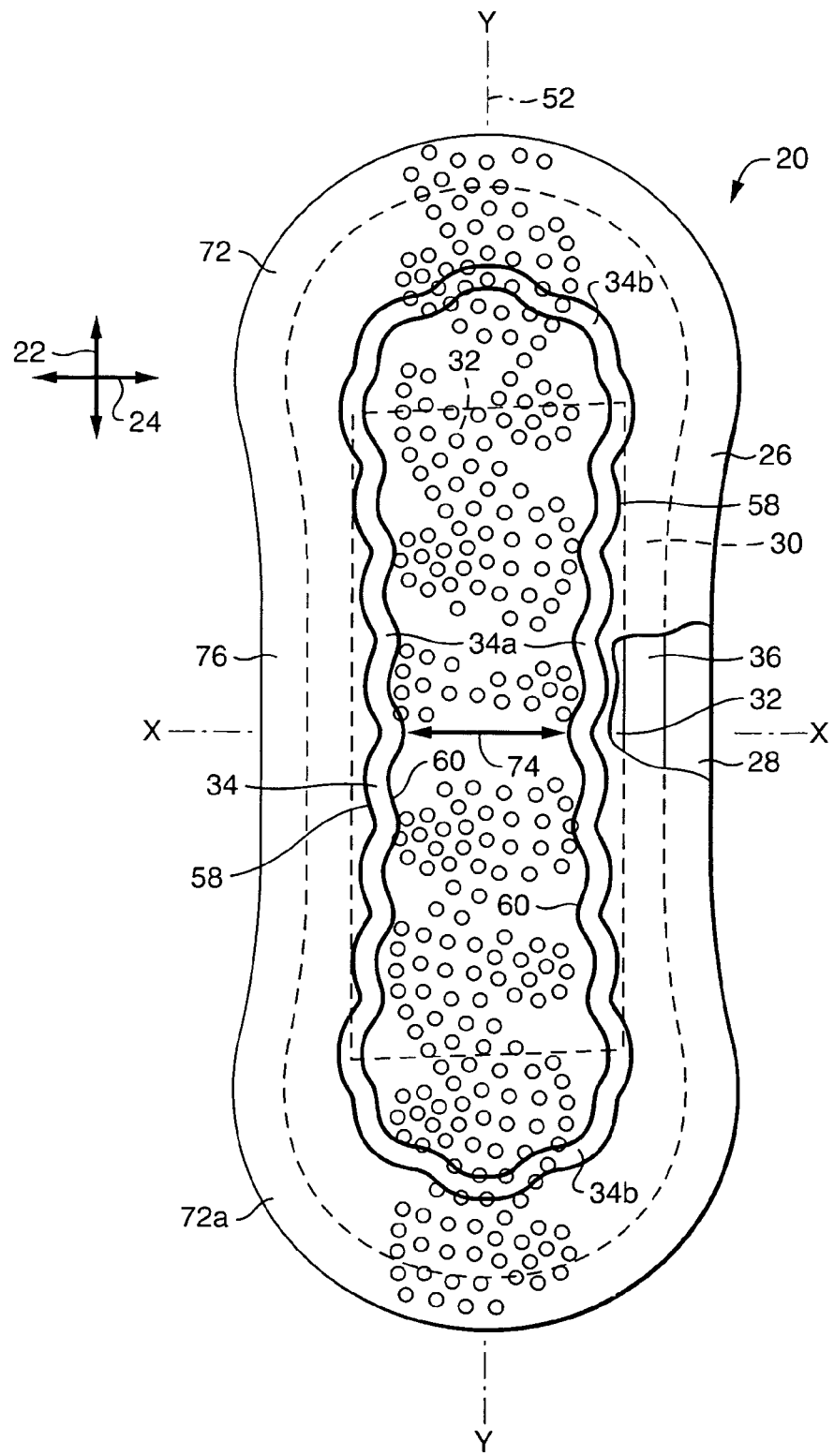
FIG. 1 shows a representative, partially cut-away, top, plan view of a bodyside of a feminine care article having a nonlinear embossment region.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, a body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 1A:
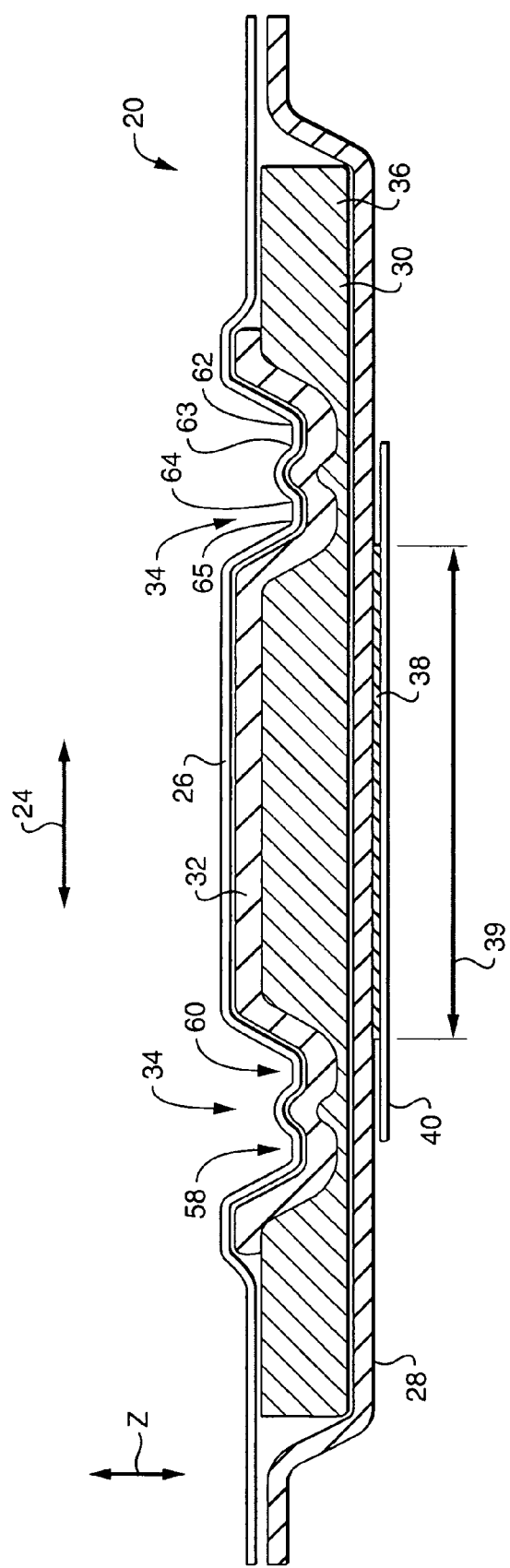
FIG. 1A shows a representative view of a transverse cross-section through an article having a nonlinear embossment region.
Figure 1B:
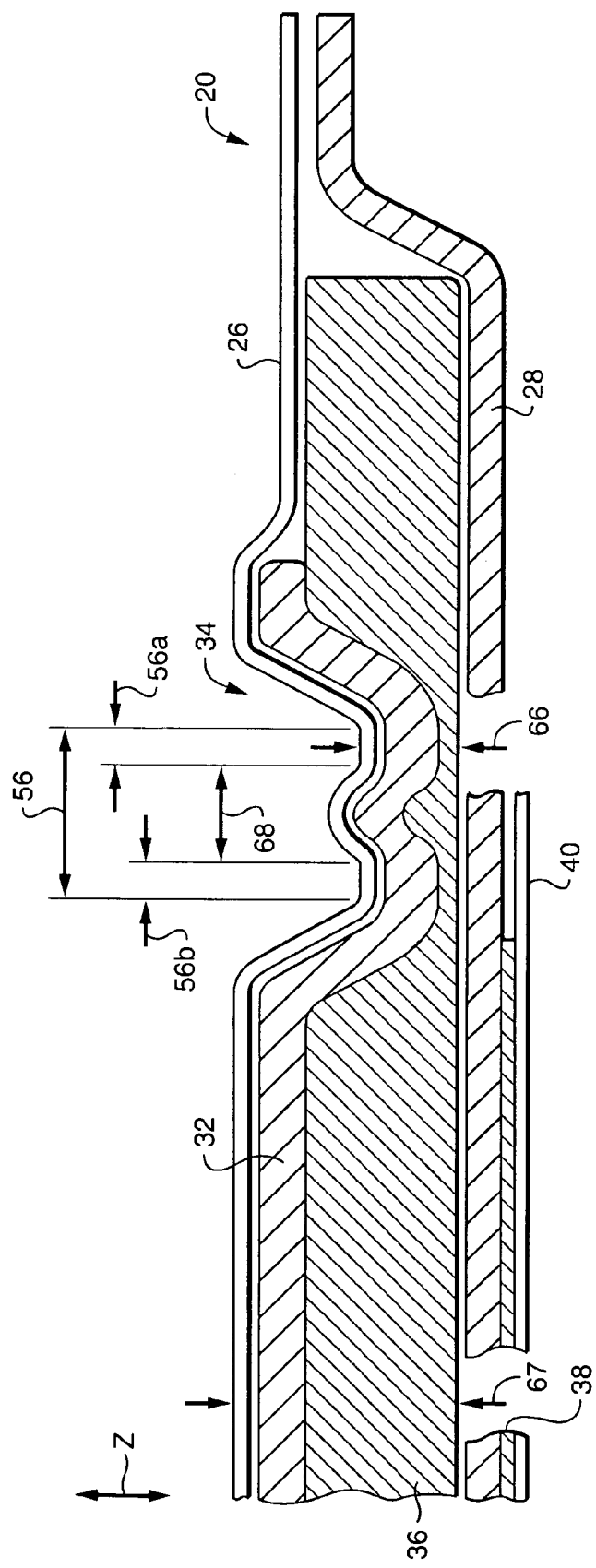
FIG. 1B shows a representative enlarged, partially cut-away view of a portion of a transverse cross-section through an article having a nonlinear embossment region.

FIGS. 1 through 1B, illustrate an example of a suitable article 20, such as the representatively shown feminine care article, which is configured to incorporate the present invention. The feminine care article can, for example, be a feminine care pad or napkin 20, and the article can have a lengthwise longitudinal direction 22 along an appointed y-axis of the article, a transverse, laterally extending, cross-direction 24 along an appointed x-axis of the article, first and second longitudinally opposed end portions 72 and 72a, and an intermediate portion 76 located between the end portions. As representatively shown, the longitudinal dimension of the article is relatively larger than the lateral dimension of the article. The article 20 can include a bodyside liner or cover 26, an outercover backsheet or baffle 28, and an absorbent structure 30 positioned between the cover and baffle. In desired arrangements, the cover can be liquid-permeable, and the baffle can be operatively liquid-impermeable. A curvilinear or otherwise nonlinear embossment region 34 can be formed in at least a portion of the cover 26 and the absorbent body 30. The embossment region 34 can extend generally longitudinally along the intermediate portion 76 of the article 20. In other aspects, the embossment region can include distinctive features of size and distribution, and the embossment region can include discrete embossment-elements. In still other aspects, the absorbent body structure 30 can at least include an intake layer 32 and a shaping layer 36. The intake and shaping layers can also have configurations of absorbent capacities, configurations of densities, configurations of basis weights and/or configurations of sizes which are selectively constructed and arranged to provide desired combinations of liquid intake time, absorbent saturation capacity, absorbent retention capacity, z-directional liquid distribution along the thickness dimension of the article, shape maintenance, and aesthetics.

By incorporating its various features and configurations, the article of the invention can provide an improved pattern of embossments that can better maintain their shape, and can operatively retain a more effective open-channel configuration during ordinary use. The article can provide an improved direction and control of desired liquid flow. As a result, the article can be less susceptible to premature leakage, and can provide better comfort and fit, improved protection and increased confidence to the wearer. Particular features can provide improved aesthetics and visual cues of absorbency.

The topsheet or cover 26 may include a layer constructed of any operative material, and may be a composite material. For example, the cover layer can include a woven fabric, a non-woven fabric, a polymer film, a film-fabric laminate or the like, as well as combinations thereof. Examples of a non-woven fabric include spunbond fabric, meltblown fabric, coform fabric, a carded web, a bonded-carded-web, a bicomponent spunbond fabric or the like as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a non-woven fabric material. The composite materials are typically in the form of integral sheets generally formed by the extrusion of a polymer onto a web of spunbond material. In a desired arrangement, the cover layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent structure 30). The selected arrangement of liquid-permeability is desirably present at least on an operative portion of the cover layer that is appointed for placement on the body-side of the article. The cover layer 26 can provide comfort and conformability, and can function to direct bodily exudates away from the body and toward the absorbent structure 30. In a desired feature, the cover layer 26 can be configured to retain little or no liquid in its structure, and can be configured to provide a relatively comfortable and non-irritating surface next to the body-tissues of a female wearer. The cover layer 26 can be constructed of any material which is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover more hydrophilic and more wettable to body fluids. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g. into the absorbent body structure). In a particular configuration, the surfactant can be substantially evenly distributed across at least a portion of the upper, bodyside surface of the cover 26 that overlays the upper, bodyside surface of the absorbent.

The cover 26 may be maintained in secured relation with the absorbent structure 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent structure, but can alternatively extend around the article to partially or entirely, surround or enclose the absorbent structure. Alternatively, the cover 26 and the baffle 28 can have peripheral margins which extend outwardly beyond the terminal, peripheral edges of the absorbent structure 30, and the extending margins can be joined together to partially or entirely, surround or enclose the absorbent structure.

The baffle 28 may include a layer constructed of any operative material, and may or may not have a selected level of liquid-permeability or liquid-impermeability, as desired. In a particular configuration, the backsheet or baffle 28 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the baffle 28 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The baffle material is a breathable film, which is dimple embossed and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed cell polyolefin foam. For example, closed cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide desired levels of absorbency and storage capacity, and desired levels of liquid acquisition and distribution. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber. The absorbent body may also include one or more components that can modify menses or inter-menstrual liquids.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as the Dow Chemical Company and Stockhausen, Inc. The superabsorbent material may desirably be included in an appointed storage or retention portion of the absorbent system, and may optionally be employed in other components or portions of the absorbent article.

In desired configurations, the absorbent body 30 can be included in a feminine care article, and can provide a total, overall absorbent saturation capacity which is at least a minimum of about 5.5 grams of menses simulant (5.5 g). The overall saturation capacity can alternatively be at least about 25 g, and can optionally be at least about 40 grams of menses simulant to provide improved performance. In a desired arrangement the total saturation capacity of the absorbent body 30 can be up to about 107 grams of menses simulant, or more.

A suitable menses simulant is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. Alternatively, a substantially equivalent device or system may be employed.

The specific saturation capacity and the specific retention capacity can be determined by soaking a 1 inch by 1 inch (2.54 cm×2.54 cm) sample of absorbent material in an amount of menses simulant that is sufficient to fully saturate the sample (e.g. 30 mL) for 30 minutes. The wet absorbent is then placed between a layer of through-air-bonded-carded web material and a layer of blotter paper, and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sampled is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample.

Accordingly:
a. Saturation Capacity=(Wet Wt. Before Centrifuge−Dry Wt.)/(Dry Wt.)
b. Retention Capacity=(Wet Wt. After Centrifuge−Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m$^2$) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb VERIGOOD white blotter paper available from Fort James Corporation, a business having offices located in Menasha, Wis., U.S.A. (e.g. product item number 411-01012). Equivalent materials may optionally be employed.

As representatively shown, the absorbent body 30 can comprise a composite structure having a selected plurality of strata or layers. With reference to FIGS. 1 through 1B, the absorbent composite can, for example, include an intake layer 32, and an absorbent shaping layer 36, as well as any other operative combination with any other desired components. As representatively shown, the structure of the absorbent body can include an absorbent pad, shaping layer 36 which is positioned between the cover 26 and the baffle 28, and can include an intake layer 32 which is positioned between the cover 26 and the shaping layer 36.

The intake layer 32 can desorb liquid from the cover 26, can help manage surges or gushes of liquid entering the article, and can help wick or otherwise distribute liquids through the absorbent structure. The intake layer can provide a temporary storage of liquid, and may provide a selected level of liquid retention.

The intake layer may include natural fibers, synthetic fibers, superabsorbent materials, a woven fabric; a nonwoven fabric; a wet-laid fibrous web; a substantially unbonded air-laid fibrous web; an operatively bonded, stabilized-airlaid fibrous web; or the like, as well as combinations thereof. Additionally, the intake layer may include a selected quantity of superabsorbent materials, as desired. In a particular aspect, the fibrous material of the intake layer can be substantially free of debonding agents. The intake layer may also include one or more components that can modify menses or intermenstrual liquid.

In a particular arrangement, the intake layer 32 can be composed of a thermally-bonded stabilized-airlaid fibrous web (e.g. Concert product code DT200.100.D0001), which is available from Concert Industries, a business having offices located in Gatineaux, Quebec, Canada.

In a desired feature, the intake layer 32 can have a relatively lower basis weight, as compared to the bottom retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36. If the basis weight and/or density difference is sufficient, improved fluid partitioning in the retention layer can be provided. An additional hydrophilic gradient may be achieved if fibers of the intake layer are configured to be more "hydrophobic" than the fibers of the retention/shaping layer due to the inclusion of debonding agents and/or polymer binders in the intake layer structure.

In particular aspects, the intake layer 32 can have a basis weight which is at least a minimum of about 30 g/m². The intake layer basis weight can alternatively be at least about 100 g/m², and can optionally be at least about 150 g/m² to provide improved performance. In other aspects, the intake layer basis weight can be up to a maximum of about 250 g/m², or more. The intake layer basis weight can alternatively be up to about 225 g/m², and can optionally be up to about 200 g/m² to provide improved performance.

If the basis weight of the intake layer 32 is outside the desired values, the article can be too thick and bulky, and can provide poor comfort and excessive awareness of the article during use. An overly high basis weight can excessively decrease the amount of liquid transferred to the shaping layer 36, can undesirably increase the amount of liquid held in the intake layer and/or can be excessively expensive. An overly low basis weight can excessively limit the ability to acquire, temporarily store and transfer liquid, and can permit premature leakage. If the basis weight of the intake layer is outside the desired values, the article can also exhibit an excessively high rewet or flowback to the wearer's skin and provide an undesired wet, moist feel to the wearer. Additionally, the intake layer can present an excessively low void volume to subsequent inputs of liquid, and the low void volume can contribute to premature leakage and excessive rewet or flowback to the wearer's skin.

In other aspects, the intake layer 32 can have a density which is at least a minimum of about 0.01 g/cm³. The intake layer density can alternatively be at least about 0.02 g/cm³, and can optionally be at least about 0.04 g/cm³ to provide improved performance. In other aspects, the intake layer density can be up to a maximum of about 0.14 g/cm³, or more. The intake layer density can alternatively be up to about 0.10 g/cm³, and can optionally be up to about 0.08 g/cm³ to provide improved performance.

If the density of the intake layer 32 is outside the desired values, the article can exhibit excessive leakage, and can provide an undesired moist, wet feeling against the wearer's skin. An overly high density can limit the saturation capacity of the intake layer and can provide excessively low permeability. This can excessively slow the acquisition and intake of liquid. Additionally, an overly high density can decrease and inhibit the desired liquid transfer to the lower, shaping layer 36. Insufficient liquid transfer can increase rewet or flowback of liquid to the wearer's skin and can decrease the void volume in the intake layer that is available to absorb a follow-up input of liquid, resulting in an increased likelihood of a premature leak. An overly low density can provide an excessively low web tensile strength, and can cause web handling problems. Depending on the basis weight, a low density can provide an excessively thick bulky intake layer that can cause poor comfort and excessive awareness of the product. A low intake layer density can also allow discrete amounts of liquid to be immobilized within the intake structure. This liquid can then be available to increase the likelihood of liquid rewet and flowback to the wearer's skin. Additionally, an overly low density intake structure can provide excessively high permeability. As a result, the properties of liquid control, spreading, distribution and temporary storage can be inadequate. The article can also allow premature leakage or an undesirably moist, wet skin.

Additionally, the intake layer 32 can have a specific, absorbent saturation capacity which is at least a minimum of about 10 grams menses simulant per gram of intake layer material (10 g/g). The specific saturation capacity of the intake layer can alternatively be at least about 10.5 g/g, and can optionally be at least about 11 g/g to provide improved performance. In other aspects, the specific saturation capacity of the intake layer can be up to a maximum of about 15 g/g, or more. The specific saturation capacity of the intake layer can alternatively be up to about 14.5 g/g, and can optionally be up to about 14 g/g to provide improved effectiveness. In a desired arrangement, the specific saturation capacity of the intake layer can be about 13 g/g.

In a further feature, the intake layer 32 can have a total, absorbent saturation capacity which is at least a minimum of about 0.5 grams of menses simulant (0.5 g). The total saturation capacity of the intake layer can alternatively be at least about 5 g, and can optionally be at least about 10 g to provide improved performance. In other aspects, the total saturation capacity of the intake layer can be up to a maximum of about 23 g, or more. The total saturation capacity of the intake layer can alternatively be up to about 22 g, and can optionally be up to about 21 g to provide improved effectiveness. In a desired arrangement, the total absorbent saturation capacity of the intake layer can be about 17 grams of menses simulant.

The top, bodyside intake layer 32 of the present invention can be equal to or smaller in size, as compared to the size of the bottom, garment-side retention/pad shaping layer 36. For example, the intake layer 32 might have a surface area that is approximately 25-50% of the surface area of the shaping layer 36. The intake layer can desirably be substantially centered (in the longitudinal direction 22 and the cross-direction 24) with respect to the shaping layer, but may optionally be skewed or offset in a selected direction (e.g. along the longitudinal direction 22), depending on where the liquid is expected to first enter the absorbent article.

The top intake layer 32 may have any operative shape and/or design. For example, the intake layer may include a single piece of material, or multiple pieces of material, such as multiple strips of material. In addition, the intake layer 32 may include holes or apertures to better provide desired liquid-intake properties. The apertures may extend partially or completely through the z-directional thickness of the intake layer 32, as desired.

In a desired configuration, the cross-directional width of the intake layer 32 can be greater than a medial spacing distance 74 between the inboard sections of the embossment region 34 that are located in the corresponding, laterally opposed side regions of the article. A capture of the intake layer by the embossment region 34 can help bond or otherwise secure the intake layer to the shaping layer 36. The inter-layer attachment can increase the product integrity and promote a controlled deformation of the absorbent article when the article is placed under side compression loads during ordinary use by the wearer.

Additionally, the intake layer 32 can be configured to exhibit a distinctive stiffness value to help provide an improved absorbent deformation when the absorbent structure is subjected to side compression loads. In a particular feature, the stiffness value of the intake layer can be at least a minimum of about 5.5 cm, as determined by a cantilever bending test. In a further feature, the stiffness value can be not more than a maximum of about 8 cm. A suitable cantilever bending test is ASTM Standard Test D 1388, with the following modification: The size of the test specimen is 1 inch×8 inch. The longer specimen allows greater accuracy when testing stiffer fabrics, since it is desirable to avoid data readings in the last inch of specimen length. If the intake layer stiffness is outside of these values, the desired product shaping may not occur.

Selected portions of the article can have target ranges for the percentage of the total absorbed liquid that is held in each of the selected portions. For example, a bodyside, top portion of the absorbent article can comprise the cover 26 and the intake layer 32, and a bottom, garment-side portion of the absorbent article can comprise the pad shaping layer 36. In a particular feature, a selected percentage of the total absorbed liquid can be retained in the shaping layer 36. When subjected to a total loading of absorbed menses simulant (e.g. a total loading of 6 grams of absorbed menses simulant), the shaping layer can hold at least a minimum of about 50% of the total loading. The shaping layer can alternatively hold at least about 60% of the total loading, and can optionally hold at least about 70% of the total loading to provide improved performance. In other aspects, the shaping layer can hold up to a maximum of about 95% of the total loading, or more. The shaping layer can alternatively hold up to about 90% of the total loading, and can optionally hold up to about 85% of the total loading to provide improved effectiveness. A desired arrangement of the bottom shaping layer 36 can be configured to retain over 75% of the total amount of absorbed liquid to improve cover dryness and in-use comfort.

When high percentages of liquid are retained in the shaping layer, however, there may be an increased risk of side leakage from the bottom, garment-side shaping layer due to a saturation of the garment-side layer in the intermediate portion of the article. The embossment regions 34 formed in the lateral side sections of the pad shaping layer can retard liquid transfer to the product side edges and can promote a wicking or other transfer of the liquid to the article end regions 72. The liquid transfer can help reduce the probability of leakage at a given liquid loading.

Accordingly, the shaping layer 36 can provide a desired, absorbent retention function and can provide liquid retention and product shaping. The shaping layer can also provide an improved resistance to bunching and twisting.

The shaping layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer can include a selected quantity of superabsorbent materials. In a particular aspect, the fibrous material of the shaping layer can be substantially free of debonding agents. In other aspects, the fibrous shaping layer may include a friction-reducing material, which can help increase the flexibility of the article in the embossment regions 34. The shaping layer may also include one or more components that can modify menses or inter-menstrual liquids In a particular arrangement, the shaping layer 36 can include a fibrous, non-debonded, southern pine kraft woodpulp (e.g. NB 416), which is available from Weyerhaeuser, a business having offices located in Federal Way, Wash., U.S.A. In another arrangement, the shaping layer can include a fibrous woodpulp treated with an agent that helps enable densification and helps reduce stiffness (e.g. ND 416; which is also available from Weyerhaeuser).

In particular aspects for regular capacity and "long-maxi" articles, the shaping layer 36 can have an average basis weight which is at least a minimum of about 150 g/m$^2$. The shaping layer basis weight can alternatively be at least about 300 g/m$^2$, and can optionally be at least about 350 g/m$^2$ to provide improved performance. In other aspects, the shaping layer basis weight can be up to a maximum of about 700 g/m$^2$, or more. The shaping layer basis weight can alternatively be up to about 600 g/m$^2$, and can optionally be up to about 550 g/m$^2$ to provide improved effectiveness.

For high capacity and overnight products the shaping layer 36 can have an average basis weight which is at least a minimum of about 400 g/m$^2$. The shaping layer basis weight can alternatively be at least about 500 g/m$^2$, and can optionally be at least about 600 g/m$^2$ to provide improved performance. In other aspects, the shaping layer basis weight can be up to a maximum of about 1000 g/m$^2$, or more. The shaping layer basis weight can alternatively be up to about 900 g/m$^2$, and can optionally be up to about 800 g/m$^2$ to provide improved performance.

The pad shaping layer 36 can be configured to have a higher proportion of its absorbent material concentrated at or near the center of the article. This can provide increased absorbent capacity in the target intake area, while maintaining a relatively low average basis weight and a relatively high flexibility along the periphery of the shaping layer. The ratio of the center basis weight to the edge or end basis weights can be within the range of about 1.05-2.0. The basis weight ratio can alternatively be within the range of 1.1-1.5, and can optionally be within the range of about 1.2-1.3 to provide improved performance.

In other aspects, the shaping layer 36 can have an average density which is at least a minimum of about 0.05 g/cm$^3$. The shaping layer density can alternatively be at least about 0.06 g/cm$^3$ to provide improved performance. In other aspects, the shaping layer density can be up to a maximum of about 0.2 g/cm$^3$, or more. The shaping layer density can alternatively be up to about 0.15 g/cm$^3$, and can optionally be up to about 0.09 g/cm$^3$ to provide improved effectiveness.

The shaping layer 36 can be also be configured such that the center of the shaping layer is relatively denser than the ends or edges. This can provide an improved density gradient within the shaping layer itself, and can provide an improved density gradient between the intake and shaping layers. Benefits are reduced side leakage, increased longitudinal fluid wicking, and improved surface dryness. The ratio of the center density to the edge or end densities can be within the range of about 1.05-2. The density ratio can alternatively be within the range of about 1.3-1.9, and can optionally be within the range of about 1.4-1.8 to provide improved performance.

Additionally, the shaping layer 36 can have a specific, absorbent saturation capacity which is at least a minimum of about 1 gram menses simulant per gram of shaping layer material (1 g/g). The specific saturation capacity of the shaping layer can alternatively be at least about 5 g/g, and can optionally be at least about 10 g/g to provide improved performance. In other aspects, the specific saturation capacity of the shaping layer can be up to a maximum of about 30 g/g, or more. The specific saturation capacity of the shaping layer can alternatively be up to about 25 g/g, and can optionally be up to about 20 g/g to provide improved effectiveness. In a desired arrangement, the specific absorbent saturation capacity of the shaping layer can be about 13 g/g, or can be about 15 g/g when the shaping layer includes a targeted 15% by weight add-on of particulate superabsorbent.

In a further feature, the shaping layer 36 can have a total, absorbent saturation capacity which is at least a minimum of about 5 grams of menses simulant (5 g). The total saturation capacity of the shaping layer can alternatively be at least about 20 g, and can optionally be at least about 30 g to provide improved performance. In other aspects, the total saturation capacity of the shaping layer can be up to a maximum of about 200 g, or more. The total saturation capacity of the shaping layer can alternatively be up to about 180 g, and can optionally be up to about 150 g to provide improved effectiveness. In a desired arrangement, the total saturation capacity of the shaping layer can be about 90 grams of menses simulant, or can be about 105 g when the shaping layer includes a targeted 15% by weight add-on of particulate superabsorbent.

The amount of superabsorbent material in a selected layer or other component (for example, the shaping layer 36) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the shaping layer may be inhibited or the product may have an inadequate rate of liquid intake, causing leakage and excessive wetness against the wearer's skin. The manufacturing costs can also become excessive.

In a particular feature, the intake layer may be operatively secured to the cover 26 with a selected distribution of adhesive. For example, the intake-layer adhesive may be applied with a slot coating operation, and the adhesive can be positioned between the cover 26 and the intake layer 32. The add-on of the intake-layer adhesive can be at least a minimum of about 0.5 g/m$^2$. The adhesive add-on can alternatively be at least about 1 g/m$^2$, and can optionally be at least about 1.5 g/m$^2$ to provide improved performance. In other aspects, the adhesive add-on can be up to a maximum of about 9 g/m$^2$, or more. The adhesive add-on can alternatively be up to about 4 g/m$^2$, and can optionally be up to about 2.5 g/m$^2$ to provide improved effectiveness.

The laminated cover 26 and intake layer web may further be operatively secured to the pad shaping layer with a selected distribution of adhesive. For example, the shaping layer adhesive may be applied with a non-contact spray operation. The adhesive may be applied as longitudinally extending lines, longitudinally orientated laterally attenuated lines, swirls, random fibers or the like, as well as combinations thereof. The adhesive can be located between the cover and the shaping layer 36, and between the intake layer 32 and the shaping layer. The add-on amount of the shaping-layer adhesive can be at least a minimum of about 3 g/m$^2$. The adhesive add-on can alternatively be at least about 6 g/m$^2$, and can optionally be at least about 9 g/m$^2$ to provide improved performance. In other aspects, the adhesive add-on can be up to a maximum of about 15 g/m$^2$, or more, to provide improved effectiveness.

If the amounts of adhesive add-on are outside the desired values, the cover, intake layer and/or shaping layer can excessively delaminate from the embossment regions 34. There can also be a poor transfer of liquid between the cover, intake and pad shaping layers. As a result, the article can exhibit premature leakage, and can exhibit an excessive bunching and twisting due to a delamination of the component layers.

The shaping layer 36 may be individually embossed with a supplemental pattern of conventional embossments to reduce the initial stiffness of the product when the product is subjected to side compression forces. In a desired configuration, for example, an array of interconnected embossment lines can be employed to create a diamond embossment pattern. The embossment lines can be arranged in a more lateral than longitudinal orientation. For example, the embossment lines can be oriented about 35 degrees from the lateral axis, and immediately adjacent lines can be spaced about 12 mm apart along the longitudinal direction. Additionally, each embossment line can be about 1 mm wide. The supplemental embossments can cooperate with the primary, nonlinear embossment region or regions 34 to help provide a more consistent deformation and shaping of the article 20 to better conform to the contours of the wearer's body.

Figure 4:
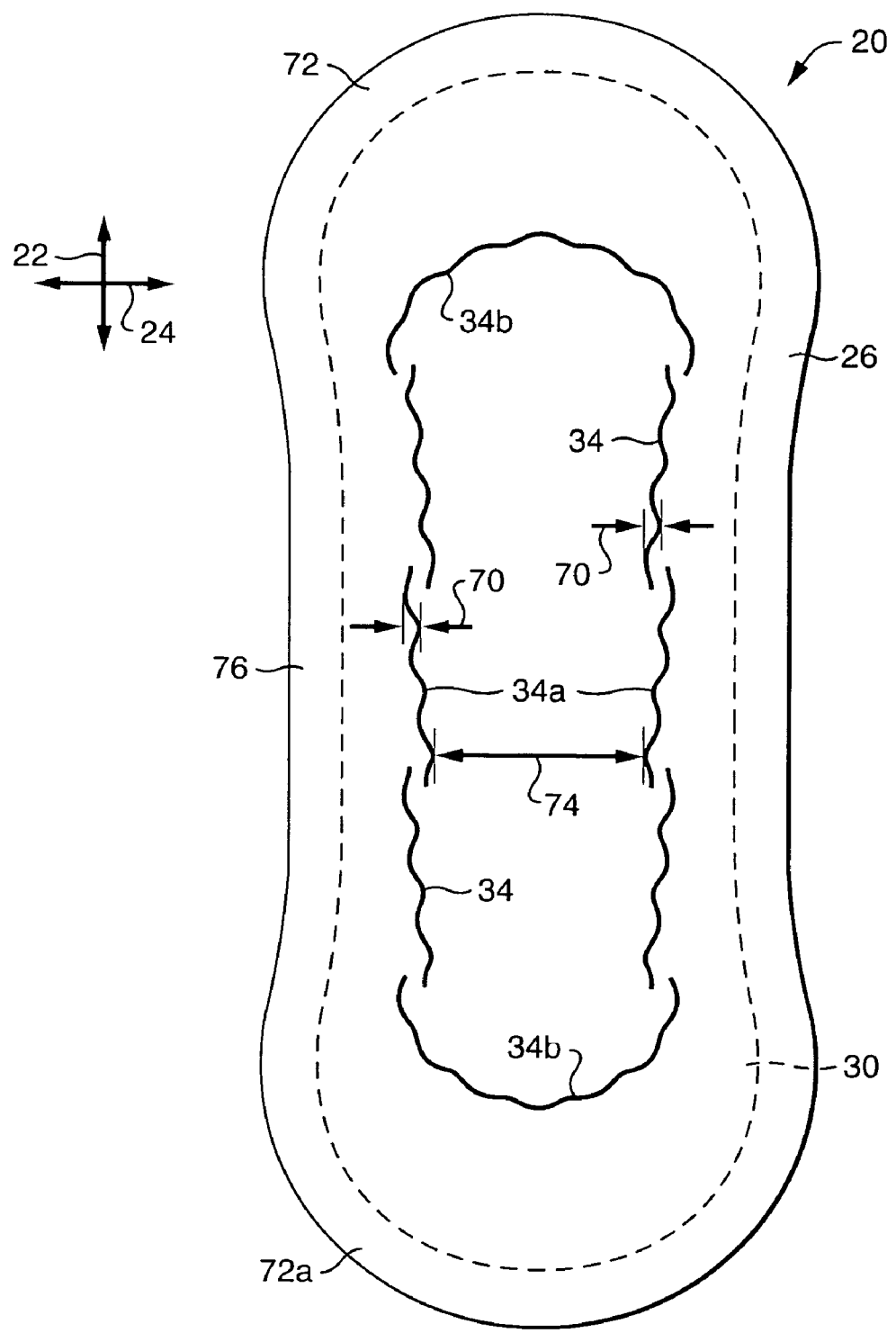
FIG. 4 shows a representative top, plan view of a bodyside of a feminine care article having a nonlinear embossment region with a discontinuous arrangement.

The embossment region 34 can be arranged in a regular or irregular pattern or array. The selected pattern or array can be discontinuous (e.g. FIG. 4) or substantially continuous. In addition, the embossments 34 can be formed in the cover 26 and in at least a portion of the bodyside of the absorbent body 30. It should be readily appreciated that the article 20 can include a plurality of two or more embossment regions 34, as desired, and each curvilinear or otherwise nonlinear embossment region 34 can operatively provide a corresponding curvilinear or otherwise nonlinear channel. The channel can help block the movement of liquid that is flowing toward a corresponding terminal side edge of the absorbent body 30, and can help direct liquid toward the end regions 72 of the article. In the embossment regions, the corresponding material or materials of the article are operatively compressed and substantially permanently deformed along the z-directional thickness of the article. The corresponding material or materials in the embossment region are operatively molded to form a desired channel structure, and are substantially uncut.

By incorporating distinctive features, the article can more effectively resist collapsing to maintain an open condition of the embossed channel regions. Additionally, the article can better provide a desired controlled deformation of the absorbent structure, and can resist and control any pivoting or hinging action that may occur along the location of the embossment region. The collapsing or hinging action can excessively close the channel or channels provided by the embossment region 34. A closing of the channel structure can undesirably allow liquids to bridge over the embossment region, and can undesirably reduce the ability to move liquid toward the end regions of the article. The increased resistance to the hinging action can help provide an article shape or profile during use which better conforms to the wearer's body and is more comfortable. The embossment region can also improve the integrity of the absorbent body, can improve the attachment between any separately provided absorbent components, and can help reduce the undesired bunching and roping of the absorbent components. For example, the embossment region 34 can improve and/or maintain the desired attachment between the intake layer 32 and the shaping layer 36. Additionally, the embossment region can be more efficiently and more effectively produced during high-speed manufacturing operations.

With reference to FIGS. 1, 2, 3, 4 and 5, the nonlinear embossment region 34 can extend over a distance of at least 4 cm along the longitudinal direction 22 across the intermediate portion 76 of the article 20, and may extend over a longitudinal distance of at least about 5 cm. The embossment region 34 can desirably extend longitudinally at least about 6 cm, and can more desirably extend longitudinally at least about 10 cm across the intermediate portion of the article. Generally stated, the intermediate portion 76 is the middle 34 percent (%) of an overall, longitudinal length of the article 20. In a further aspect, the embossment region can extend substantially continuously across the selected longitudinal distance in the intermediate portion of the article. Additionally, the curvilinear or otherwise nonlinear embossment region 34 can extend at least partially across the first and/or second end portions 72, 72a of the article.

As representatively shown, the embossment region 34 can have a pair of transversely spaced-apart, laterally opposed side-portions 34a which extend generally along the longitudinal-direction 22 at locations that are generally adjacent a pair of laterally opposed side edges of the absorbent body 30. Additionally the embossment region 34 can include a longitudinally opposed pair of end-portions 34b, and at least a part of the end-portions can extend generally laterally along the cross-direction 24 at positions that are generally adjacent a pair of longitudinally opposed end edges of the absorbent body. Either or both of the side-portions can be configured to include the various features and aspects attributed to the embossment region. Similarly, either or both of the end-portions may include desired features and aspects of the embossment region 34.

The side-portions and end-portions of the embossment region 34 can desirably be configured to provide a desired outline shape, and the embossment region can extend along at least the bodyside of the article to provide the desired shape. The embossment region may also extend along the garment-side surface of the absorbent body 30. In particular examples, the path of the embossment region may provide a symmetrical shape, an asymmetrical shape, a regular or irregular rectilinear shape, a regular or irregular curvilinear shape or the like, as well as combinations thereof. The embossment region may be configured to be discontinuous or substantially continuous, as desired. In particular arrangements; the embossment region 34 can be arranged to effectively provide a substantially closed-shape. In other desired configurations, the embossment region 34 can be located proximate to and relatively inboard from a perimeter edge of the absorbent body 30, and in a particular aspect can extend along substantially an entirety of the absorbent body perimeter.

Figure 2:
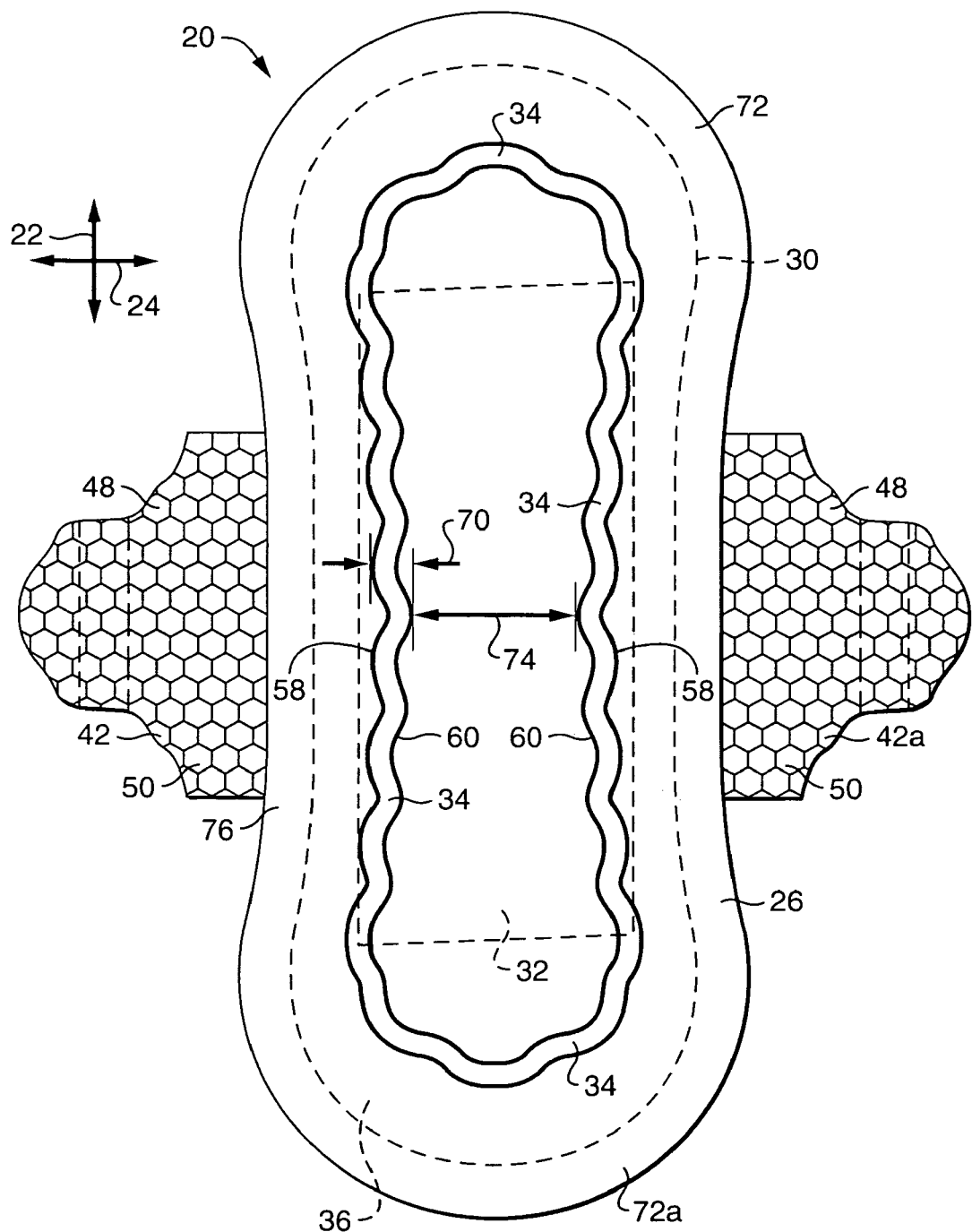
FIG. 2 shows a representative, partially cut-away plan view of a bodyside of a feminine care article in which side-panel portions are arranged in a laterally-extended position.

The curvilinear or otherwise nonlinear embossment region 34 can have a distinctive traversing distance 70, as representatively shown in FIG. 2. The traversing distance 70 can be present at least along the intermediate portion 76 of the article, and extends generally along the lateral cross-direction 24. As representatively shown, the embossment region 34 can have back-and-forth pattern-shape which can extend over a selective lateral traversing distance 70. The back-and-forth shape can, for example, include an undulating pattern, a serpentine pattern, a zig-zag pattern, a generally sinusoidal pattern, a cycloidal pattern, a semi-cycloidal pattern, a wavy pattern or the like, as well as combinations thereof. The lateral traversing distance 70 can be determined by measuring the lateral distance between the most-outboard-edge to the most-inboard-edge of the nonlinear embossment region 34, as observed during a back-and-forth cycle of the selected, nonlinear embossment pattern. The selected nonlinear pattern can extend a distance of at least 4 cm along the longitudinal direction 22 within the intermediate portion 76 of the article. As previously discussed, the back-and-forth nonlinear pattern can optionally extend across a selected longitudinal distance within the article intermediate portion 76.

In a particular aspect, the lateral traversing distance 70 can be at least a minimum of about 0.1 cm. The lateral traversing distance can alternatively be at least about 0.2 cm, and can optionally be at least about 0.3 cm to provide improved performance. In other aspects, the lateral traversing distance can be up to a maximum of about 2.3 cm, or more. The lateral traversing distance can alternatively be up to about 1.5 cm, and can optionally be up to about 1.1 cm to provide improved effectiveness. A desired arrangement can include a traversing distance which is within the range of about 0.7-0.8 cm.

If the traversing distance 70 is outside the desired values, there can be an excessive pivoting or hinging action along the embossment region. Additionally, there can be an excessive collapsing of the channel structure. Embossments which traverse beyond the desired values may also result in undesirable stiffness in the product edges and inadequate fit due to an insufficient medial spacing distance 74 between the inboard edges of the laterally opposed sections of the embossment region.

The curvilinear embossment region 34 can have a distinctive frequency of its traversing occurrence. As representatively shown in FIGS. 1, 4 and 5, each traversing occurrence can include a single back-and-forth cycle and the pattern array selected for the curvilinear embossment region 34. The occurrence of the traversing cycles may be present in an irregular, non-repeating pattern, in a substantially regular, repeating pattern or in a combination thereof, as desired. Additionally, the traversing frequency can occur along at least the intermediate portion 76 of the article. In particular aspects, the traversing occurrence can be at least a minimum of about 1 cycle. The traversing occurrence can alternatively be at least about 1.2 or 1.5 cycles, and can optionally be at least about 2 cycles to provide improved performance. In other aspects, the traversing occurrence can be up to a maximum of about 10 cycles, or more. The traversing occurrence can alternatively be up to about 8 cycles, and can optionally be up to about 6 cycles to provide improved effectiveness. In a further aspect, the desired number of cycles can be distributed or otherwise arranged to occur with a 5 cm, longitudinal length section of the article. If the traversing occurrence is outside the desired values or parameters, there can be an excessive pivoting or hinging action along the embossment region or an excessive collapsing of the channel structure. Traversing frequencies outside of the desired values may also degrade the aesthetics and consumer perception of the article.

Figure 4A:
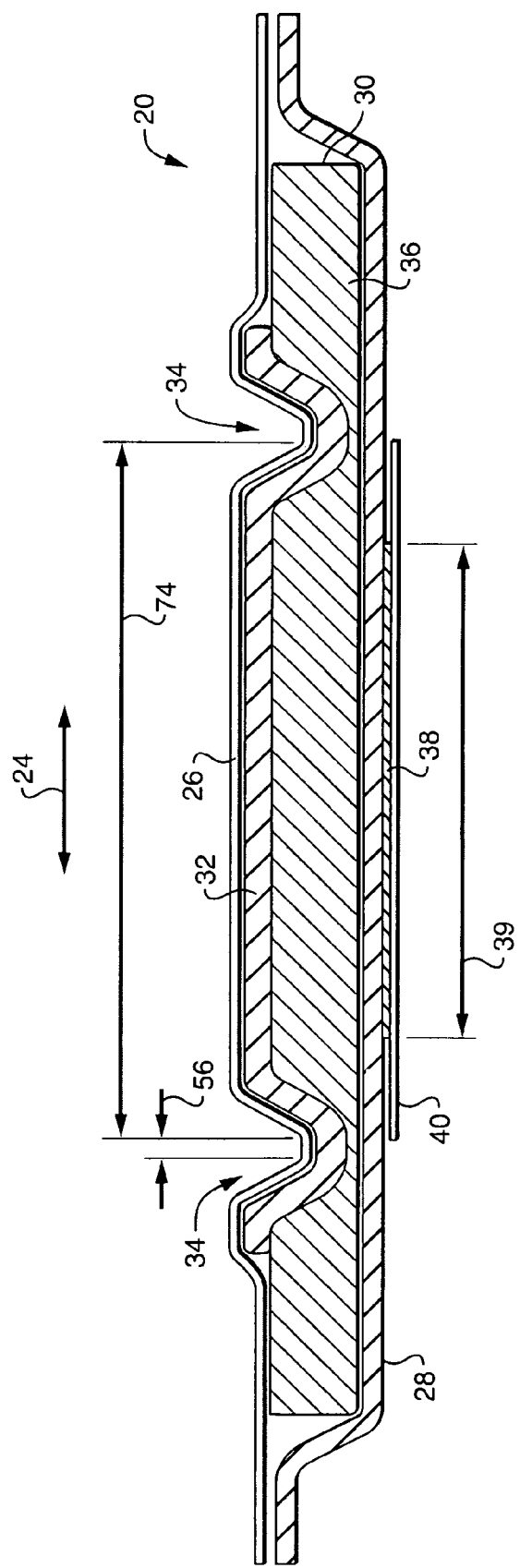
FIG. 4A shows a representative view of another transverse cross-section through an article having a nonlinear embossment region.
Figure 5:
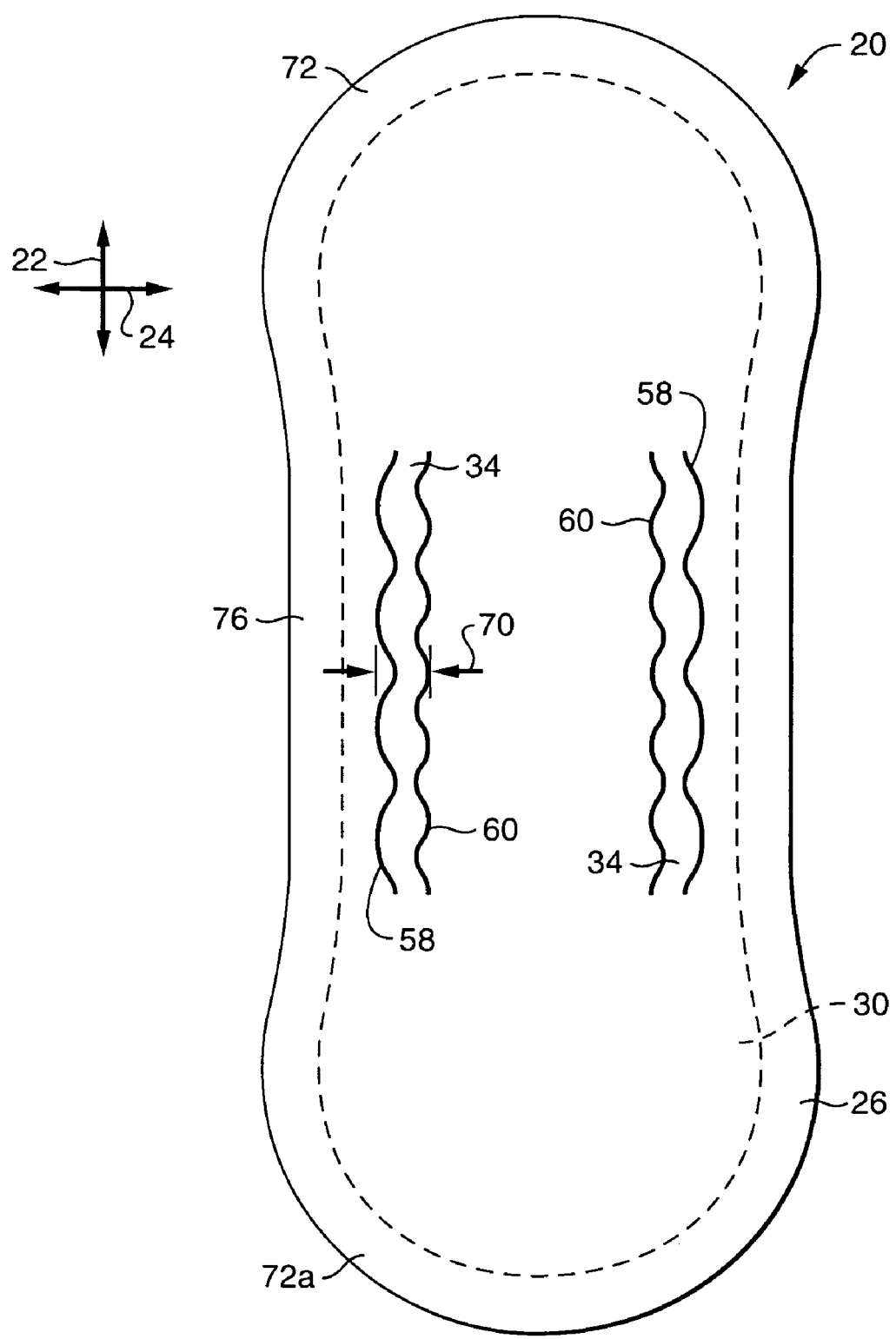
FIG. 5 shows a representative top, plan view of a bodyside of a feminine care article having a nonlinear embossment region with embossments elements arranged in a nonsynchronous configuration.

With reference to FIGS. 1A, 1B and 4A, the embossment region 34 can have a distinctive overall, region width 56 as measured between an outboard edge 62 of the embossment region 34 and a corresponding inboard edge 65 of the embossment region. In particular aspects, the embossment region width 56 can be at least a minimum of about 0.05 cm. The overall embossment region width can alternatively be at least about 0.1 cm, and can optionally be at least about 0.15 cm to provide improved performance. In other aspects, the overall embossment region width can be up to a maximum of about 0.7 cm, or more. The overall embossment region width can alternatively be up to about 0.5 cm, and can optionally be up to about 0.3 cm to provide improved effectiveness.

If the overall width of the embossment region is too low, liquid may excessively bridge over the embossment region during use, and the article may prematurely leak. Additionally, the cover and/or baffle may be excessively susceptible to cut-through during high-speed embossing operations. If the overall width of the embossment region is too large, the article may exhibit excessive stiffness.

As representatively shown in FIGS. 1 through 2, the embossment region 34 can include a plurality of two or more channel-elements or embossment-elements. In the representatively shown configuration, for example, the embossment region 34 can include a first, longitudinally-extending, curvilinear or otherwise nonlinear channel embossment-element 58. Additionally, the embossment region can include at least a second, longitudinally-extending, curvilinear or otherwise nonlinear embossment-element 60, which is located proximately adjacent the first embossment-element. The first embossment-element can have a relatively outboard position toward the terminal edges of the article, and the second embossment-element can be arranged with a relatively inboard position toward the center of the article. The channel embossment-elements may or may not be parallel. Additionally, the traversing occurrences of the embossment-elements may be substantially synchronous or in-phase (e.g. FIG. 1), or may be nonsynchronous or out-of-phase (e.g. FIGS. 4 and 5). The nonsynchronous embossment elements may also have different configurations of their nonlinear patterns, and/or may have different frequencies of occurrence. Where the embossment-elements are nonsynchronous, any or all of the individual embossment-elements may have any or all of the parameters described for the embossment region 34. For example, any or all of the individual embossment-elements may have the undulating shape, lateral traversing distance and/or traversing frequency of occurrence that are described for the embossment element 34. Desirably, each of the individual embossment-elements will operatively cooperate to exhibit the parameters desired for the embossment element 34.

With reference to FIGS. 1A and 1B, there can be a selected separation distance 68 between the proximate, immediately adjacent embossment-elements. As representatively shown, for example, a separation distance between the first and second embossment-elements 58 and 60 can be at least a minimum of about 0.05 cm. The separation distance 68 can alternatively be at least about 0.1 cm, and can optionally be at least about 0.2 cm to provide improved performance. In other aspects, the separation distance can be up to a maximum of about 0.8 cm, or more. The separation distance can alternatively be up to about 0.5 cm, and can optionally be up to about 0.3 cm to provide improved effectiveness.

If the separation distance 68 is outside the desired values, the article can exhibit excessive stiffness, and the definition of the embossment may be less readily perceived. Additionally, the desired liquid wicking along the embossment can be degraded. The article can also be less able to provide a desired controlled deformation which properly shapes to the contours of the wearer's body. If the separation distance is too large, the liquid may also excessively bridge across the embossment elements, resulting in premature leakage.

As representatively shown, the embossment region 34 can have an overall, region width 56, as measured between an outboard-edge 62 of a first embossment-element 58 and a correspondingly associated inboard edge 65 of a second embossment-element 60. In particular aspects, the embossment region width 56 can be at least a minimum of about 0.15 cm. The overall embossment region width can alternatively be at least about 0.3 cm, and can optionally be at least about 0.5 cm to provide improved performance. In other aspects, the overall embossment region width can be up to a maximum of about 2.2 cm, or more. The overall embossment region width can alternatively be up to about 1.1 cm, and can optionally be up to about 0.7 cm to provide improved effectiveness.

If the overall width of the embossment region is too low, liquid may excessively bridge over the embossment region during use, and the article may prematurely leak. Additionally, the cover and/or baffle may be excessively susceptible to cut-through during high-speed embossing operations. If the overall width of the embossment region is too large, the article may exhibit excessive stiffness.

With reference to FIG. 1B, the first embossment-element 58 can have a first embossment-element width 56a and the second embossment-element 60 can have a second embossment-element width 56b. In a particular feature, the first embossment-element width 56a can be at least a minimum of about 0.05 cm. The first embossment-element width can alternatively be at least about 0.08 cm, and can optionally be at least about 0.1 cm to provide improved performance. In other aspects, the first embossment-element width 56a can be up to a maximum of about 0.7 cm, or more. The first embossment-element width can alternatively be up to about 0.3 cm, and can optionally be up to about 0.2 cm to provide improved effectiveness.

Additionally, the second embossment-element width 56b can be at least a minimum of about 0.05 cm. The second embossment-element width can alternatively be at least about 0.08 cm, and can optionally be at least about 0.1 cm to provide improved performance. In other aspects, the second embossment-element width 56b can be up to a maximum of about 0.7 cm, or more. The second embossment-element width can alternatively be up to about 0.3 cm, and can optionally be up to about 0.2 cm to provide improved effectiveness.

If the embossment-element width 56a and/or 56b is too large, the product can exhibit excessive stiffness. If the embossment-element width 56a and/or 56b is too small, liquid may excessively bridge across the embossment region to cause premature leakage. Additionally, the cover and/or baffle materials in the embossment region may be excessively susceptible to cut-through during the embossing operation.

In still another feature, the embossment region 34 can have an embossment caliper 66 which is a relatively small percentage of a central caliper 67 of the article. In a particular aspect, the caliper of the embossment region 34 can be at least a minimum of about 5% of the caliper of the unembossed central region of the article. The embossment caliper can alternatively be at least about 8% of the caliper of the central region, and can optionally be at least about 12% of the central caliper to provide improved performance. In other aspects, the embossment caliper can be up to a maximum of about 37 of the caliper of the unembossed central region of the article, or more. The embossment caliper can alternatively be up to about 30% of the caliper of the central region, and can optionally be up to about 23% of the central caliper to provide improved effectiveness.

The central caliper is determined at the intersection of the longitudinal and transverse centerlines of the article, and the embossment caliper percentage is determined by the following formula:

$$\text{Embossment caliper percentage} = 100 \times (\text{embossment caliper}/\text{central caliper}).$$

The caliper measurements should exclude the thickness of the backsheet or baffle 28, and should exclude the thickness of any components that are layered onto the garment-side surface of the backsheet or baffle. In the shown arrangement, for example the caliper values exclude the thicknesses of the baffle 28, the garment adhesive 38 and the release layer 40.

The caliper measurements can be optically determined from product cross-sections using the QUANTIMET 600 Image Analysis System (available from Leica, Inc., a business having offices located in Cambridge, United Kingdom) equipped with QWIN version 1.06A software. Transverse cross-sections of the product were created by cryogenically freezing the article with liquid nitrogen, and transversely cutting the article into sections 1 cm wide (width measured along the longitudinal direction 22) using a BERKEL Commercial Food Processing Machine—Model #909, which is available from Berkel Incorporated, a business having offices located in LaPorte, Ind., U.S.A.

If the embossment caliper percentage is outside the desired values, the article may exhibit excessive leakage, and the article may not properly deform to match wearer's body contours. Additionally, component layers, such as the cover, intake layer and/or shaping layer, can be inadequately secured together. The inadequate securement can allow excessive bunching and twisting of the absorbent structure.

With reference again to FIGS. 1 through 1B, the absorbent body 30 can include an intake layer 32 and a shaping layer 36. Additionally, the embossment region 34 can be formed into the cover 26, the intake layer 32 and the shaping layer 36 at least along the intermediate portion 76 of the article 20. In a further feature, the embossment region 34 can be formed into the cover 26 and the shaping layer 36 along at least a portion of either or both of the end portions 72, 72a of the article 20.

In optional arrangements, the article 20 may include additional components or component layers, as desired. For example, a transfer layer may be positioned between the intake layer 32 and the shaping layer 36. Additionally, a selected configuration of garment adhesive 38, such as one or more strip regions, may be distributed onto the garment-side of the article to help secure the article to a wearer's undergarment. Typically, the garment adhesive is distributed over the garment-side of the baffle, and one or more layers or sheets of release material 40 are removably placed over the garment adhesive to cover the adhesive for storage prior to use.

Figure 2A:
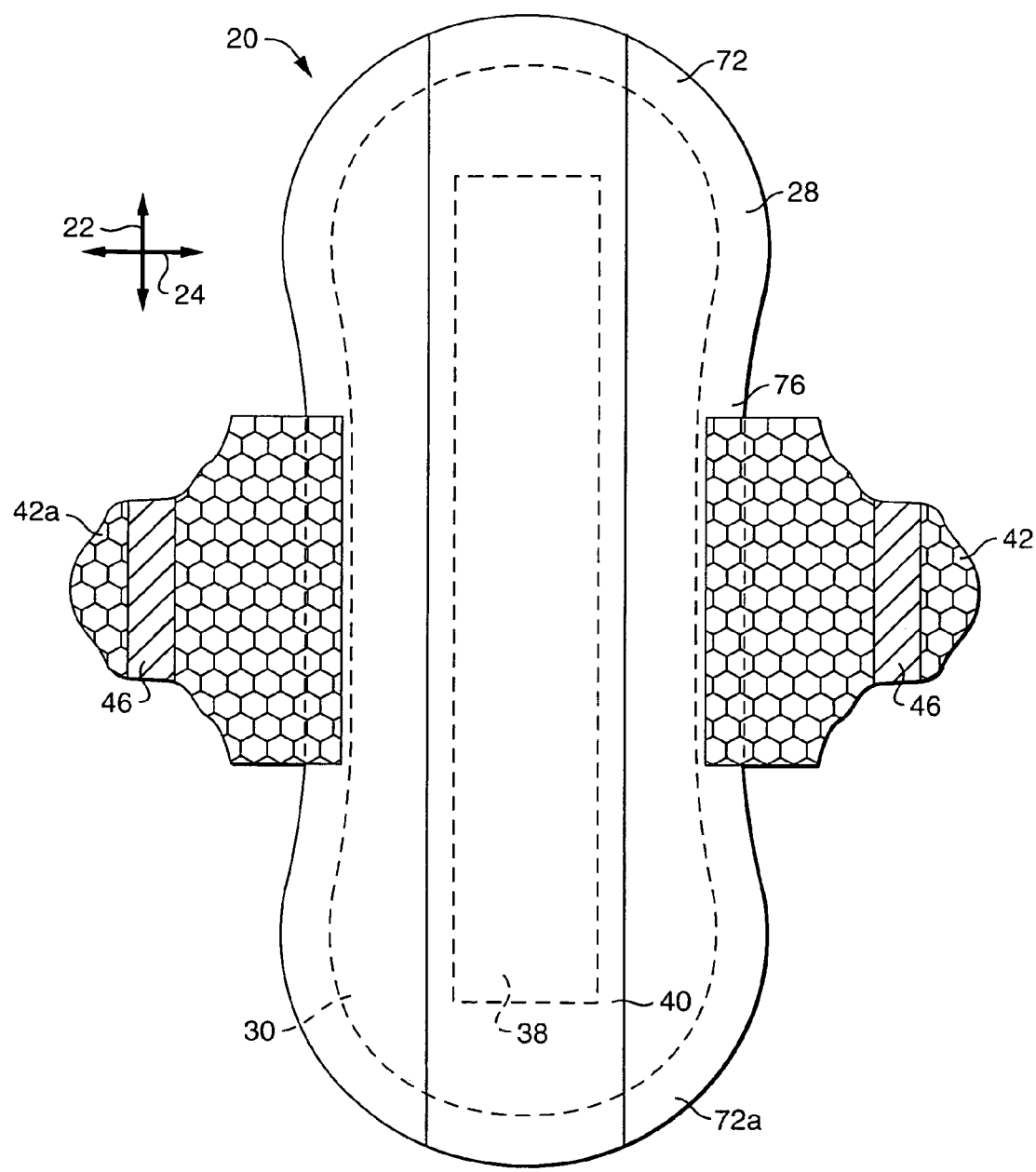
FIG. 2A shows a representative, partially cut-away plan view of a garment-side of a feminine care article in which side-panel portions are arranged in a laterally-extended position.
Figure 2B:
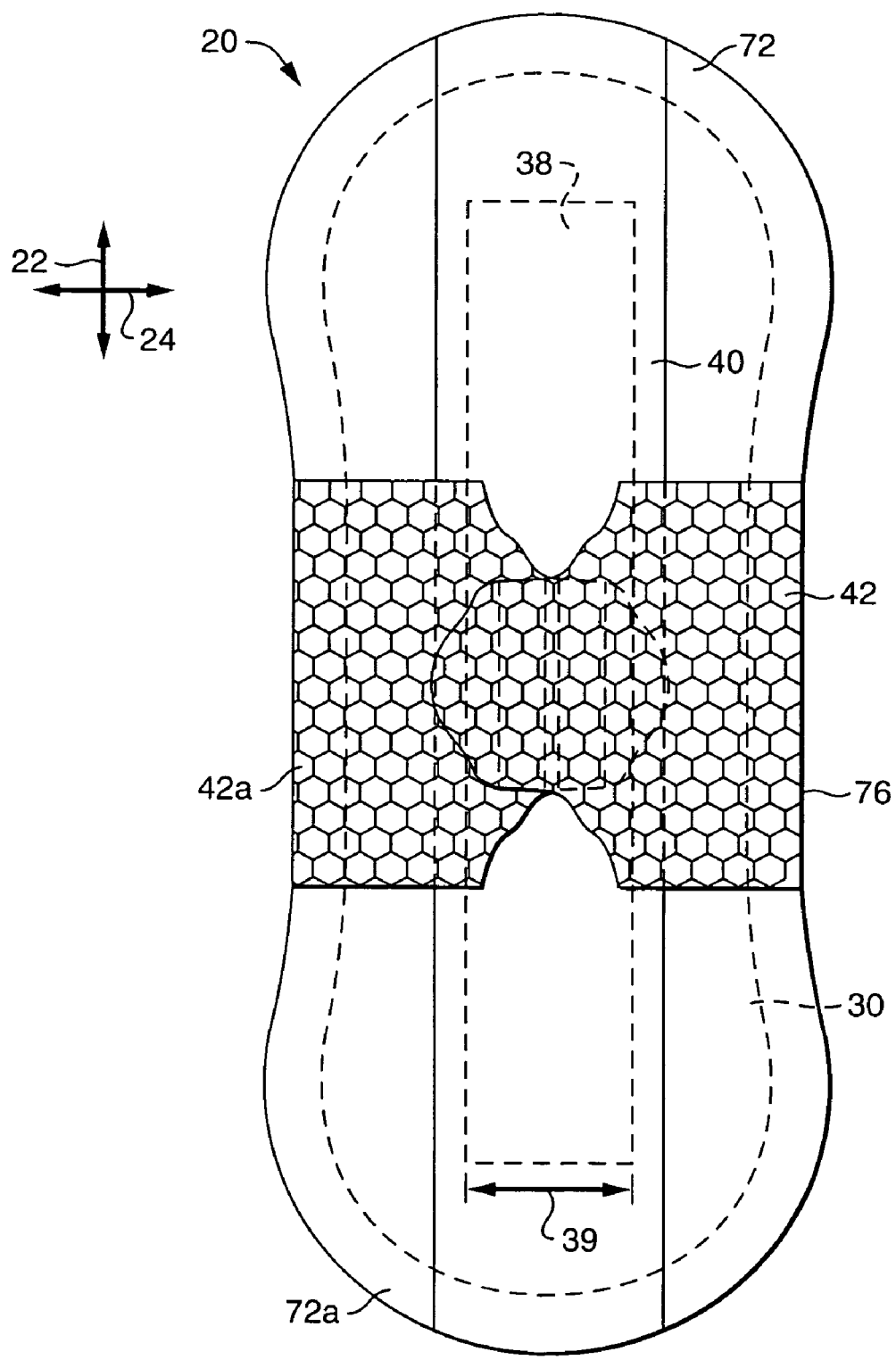
FIG. 2B shows a representative plan view of a garment-side of a feminine care article in which side-panel portions are arranged in a closed position.
Figure 3:
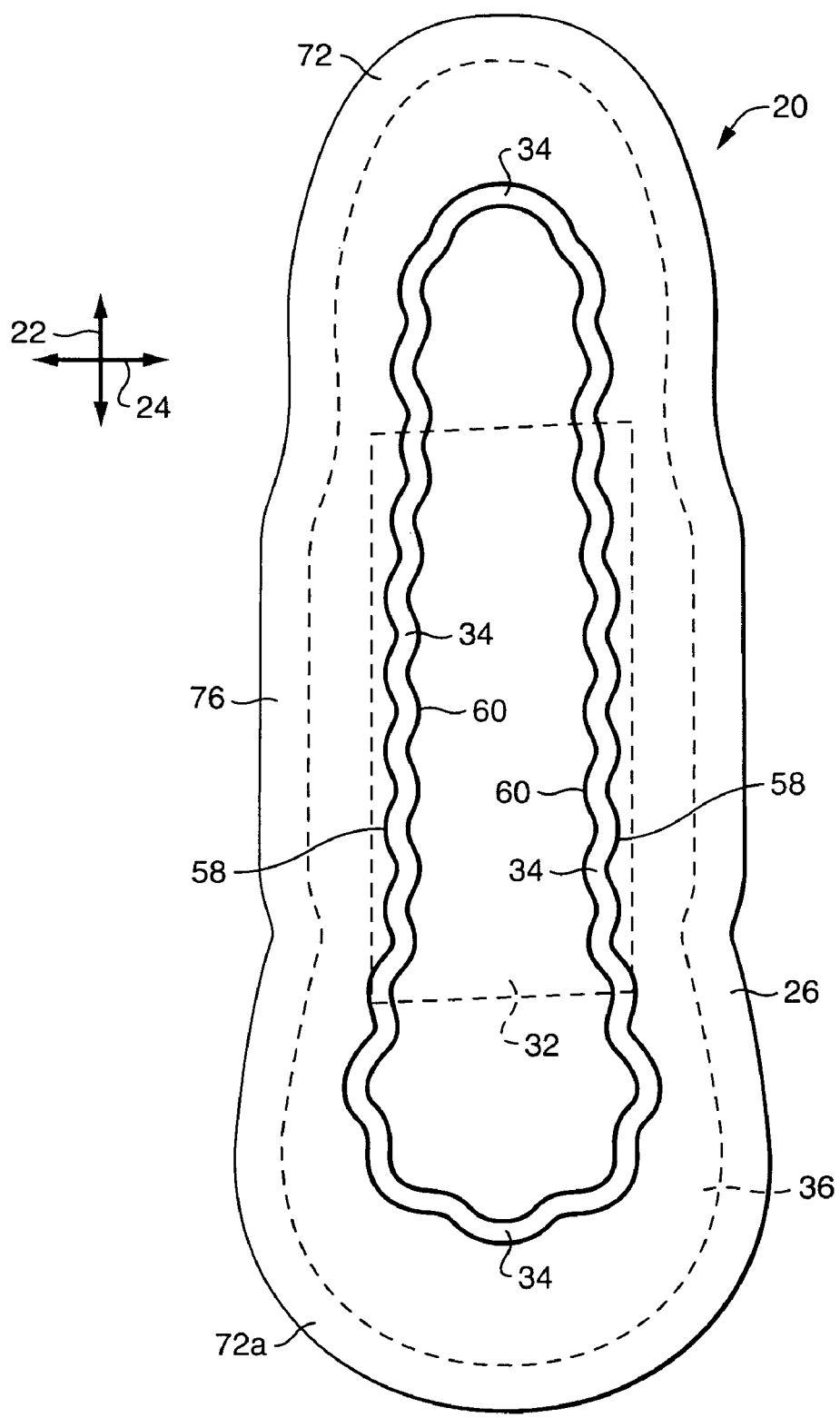
FIG. 3 shows a representative top, plan view of a bodyside of a feminine care article having a different shape and having a nonlinear embossment region with a different layout shape of the embossment region.

In a particular feature, the garment adhesive can have a distinctive overall, cross-directional width 39 (e.g. FIGS. 1A and 2B). The garment adhesive width should have a cross-directional width which is less than or equal to the cross-directional, medial spacing distance 74 between the most inboard edges of the portions of the embossment regions 34 that extend along opposed, lateral sides of the article.

In particular aspects, the garment adhesive width can be at least a minimum of about 1.5 cm. The garment adhesive width can alternatively be at least about 2 cm, and can optionally be at least about 2.5 cm to provide improved performance. In other aspects, the garment adhesive width can be up to a maximum of about 5 cm, or more. The garment adhesive width can alternatively be up to about 3.5 cm, and can optionally be up to about 3 cm to provide improved effectiveness.

If the width of the garment adhesive is outside the desired values, the article may exhibit a poor attachment to the wearer's undergarment, and may undesirably adhere to the wearer's body. An overly wide garment adhesive can also interfere with the desired shaping and conformance of the article to of the contours of the wearer's body. Additionally, the garment adhesive may inhibit the formation of the desired embossment region 34 during high-speed manufacturing.

The article 20 can include a system of side-panel or wing portions 42. The side-panels can be unitarily formed from a selected component of the article, such as the cover and/or the baffle, and are integrally connected to appointed sections of the side regions along the intermediate portion 76 of the article. Alternatively, the side-panels or wings can be separately provided members that are subsequently attached or otherwise operatively joined to the intermediate portion of the article 20 (e.g. FIGS. 2 through 2B).

The side-panels can have an appointed storage position (e.g. FIG. 2B) in which the side-panels 42 are directed generally inwardly toward the longitudinally-extending centerline 52. As illustrated, the side-panel that is connected to one side margin may have sufficient cross-directional length to extend and continue past the centerline 52 to approach the laterally opposite side margin of the article. The storage position of the side-panels can ordinarily represent an arrangement observed when article is first removed from its wrapper or other packaging. Prior to placing the article into a bodyside of an undergarment prior to use, the side-panels 42 can be selectively arranged to extend laterally from the side regions of the article intermediate portion 76 (e.g. FIGS. 2 and 2A). After placing the article in the undergarment, the side-panels 42 can be operatively wrapped and secured around the side edges of the undergarment to help hold the article in place.

The side-panel portions 42 can have any operative construction, and can include a layer of any operative material. Additionally, each side-panel can comprise a composite material. For example, the side-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region of the article in any operative manner. For example, the side-panel can be joined to the cover 26, the baffle 28 or another article component, as well as any combination thereof. In the illustrated example, each side-panel 42 is joined to the outward, garment-side surface of the baffle 28, but may optionally be joined to the bodyside surface of the baffle. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component which is operatively joined to an appointed engagement surface of its associated side-panel. The panel-fastener can include a system of interengaging mechanical fasteners, a system of adhesive fasteners or the like, as well as combinations thereof.

With reference to FIG. 2A, for example, each side-panel 42 can include a hook or other "male" component 46 of an interengaging mechanical fastener system. Any operative hook component may be employed. For example, a suitable hook component materials can include a J-hook, mushroom-head hook, flat-top nail-head hook, a palm-tree hook, a multiple-J hook or the like, as well as combinations thereof. Alternatively, either or both side-panels 42 can include a panel-fastener system which incorporates an operative adhesive. The adhesive may be a solvent-base adhesive, a hotmelt adhesive, a pressure-sensitive adhesive, or the like, as well as combinations thereof.

An operative first section of the selected hook component 46 can be joined to a major facing surface of at least a first side-panel portion 42, and can be configured to contact or otherwise engage a second side-panel portion 42a during ordinary use, as representatively shown in FIG. 2B. Additionally, an operative second section of a hook component 46a, composed of the same or different type of hook material, can be joined to a major facing surface of the second side-panel portion 42a, and can be configured to contact or otherwise engage an outward surface of the wearer's undergarment during ordinary use. For example, the hook component can be arranged to operatively engage and removably attach to the outward surface of a crotch region of the undergarment.

Each side-panel portion 42, or any desired combination of the employed side-panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate or the like, as well as combinations thereof.

An operative first section of a selected loop component 48 can be joined to a major facing surface of at least the second side-panel portion 42a, and can be configured to contact or otherwise engage the hook component 46 on the first side-panel portion 42 during ordinary use. Additionally, an operative second section of a loop component 48a, composed of the same or different type of loop material, can be joined to a major facing surface of the first side-panel portion 42. As a result, the user can have the option of alternatively attaching the second hook component 46a of the second side-panel onto the second loop component 48a of the first side-panel. Accordingly, the first hook component 46 may alternatively be engaged with the outward surface of the wearer's undergarment.

Each or any desired combination of the provided loop components (48, 48a) may be a separately provided member that is subsequently joined and assembled to its corresponding side-panel portion (42a, 42). In a desired feature, each or any desired combination of the provided loop components can be integrally provided by the material employed to construct its corresponding side-panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., and granted Jan. 12, 1999; the entire disclosure of which is incorporated herein by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g, and can optionally be at least about 150 g to provide improved performance. In other aspects, the peel-force value can be up to a maximum of about 300 g, or more. The peel-force value can alternatively be up to about 250 g, and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g, and can optionally be at least about 1500 g to provide improved performance. In other aspects, the shear-force value can be up to a maximum of about 3500 g, or more. The shear-force value can alternatively be up to about 3000 g, and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

The following Examples describe particular configurations of the invention, and are presented to provide a more detailed understanding of the invention. The Examples are not intended to limit the scope of the present invention in any way. From a complete consideration of the entire disclosure, other arrangements within the scope of the claims will be readily apparent to one skilled in the art.

EXAMPLE

The Example included a two layer absorbent system assembled between a cover and a baffle. The cover was a 0.6 osy (20 g/m$^2$) basis weight, and included wettable, random laid, 3.0 denier continuous polypropylene fibers, with 2% TIO$_2$ concentrate and 0.45% AHCOVEL surfactant, which is available from Uniqema, a business having offices in New Castle, Del., U.S.A. The fibers of the cover were thermally bonded with an expanded Hanson Pennings diamond bond pattern #1 R90330-M-15D.

The baffle was composed of a 1.0 mil (0.0254 mm) thick, rose polyethylene film having a micro-embossed MFST pattern and a 37 dynes/cm Corona treatment. The baffle material was obtained from Pliant Corporation, a business having offices located in Schaumburg, Ill., U.S.A.

The absorbent structure included intake layer and an absorbent shaping layer, in accordance with the following: The intake layer had a cross-directional width of 50 mm, and was composed of a 200 g/m², 0.06 g/cm³ thermally-bonded stabilized-airlaid fibrous web obtained from Concert Industries, a business having offices located in Gatineaux, Quebec, Canada. The web contained 90% by weight Weyerhaeuser NF401 semi-treated woodpulp fluff, and 10% KoSa T255 bicomponent binder fiber. The "semi-treated" woodpulp included a debonding agent which has been added to the woodpulp fibers to improve opening and fiberization. The Weyerhaeuser NF401 semi-treated fluff pulp is available from Weyerhaeuser, a business having offices located in Federal Way, Wash., U.S.A. The KoSa T255 bicomponent binder fiber is available from KoSA, a business having offices located in Houston, Tex., U.S.A.

The shaping layer was composed of a 500 g/m² basis weight, 0.07 g/cm³ density, non-debonded, southern pine kraft woodpulp fluff, which is available as NB 416 from Weyerhaeuser, a business having offices located in Federal Way, Wash., U.S.A. The shaping layer was embossed with a diamond pattern of embossing lines (35 degree, 1 mm wide embossing lines). In the article intermediate portion 76, the shaping layer had a cross-directional width of 66 mm.

The shaping layer fluff was adhered to the cover and intake layer using 34-5610 construction adhesive, which is available from National Starch, a business having offices in Bridgewater, N.J., U.S.A. The construction adhesive was applied at a level of 9 g/m².

The nonlinear embossment region of the article had a traversing frequency of 0.5-0.6 cycles/cm across the intermediate portion of the article. The nonlinear embossments traversed a lateral distance of 0.7-0.8 cm across the intermediate region. The lateral width of the embossment region was 0.5-0.7 cm. The embossment region was composed of two continuous, synchronously arranged embossing elements of uniform and equal width spaced at a uniform distance of 0.2-0.3 cm. The embossment areas were compressed to an embossment caliper which was approximately 12-23% of the unembossed, central caliper of the article. The medial spacing distance 74 between the laterally opposed, embossment region side-portions 34a was about 29-30 mm.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An absorbent article having a longitudinal direction, a lateral direction, first and second longitudinally opposed end portions, and an intermediate portion located between the end portions, said article comprising a liquid-permeable cover;

a baffle;

an absorbent body sandwiched between said cover and baffle, the absorbent body having perimeter side-edges, perimeter end-edges, an intake layer and a shaping layer; and a nonlinear embossment region formed in at least a portion of said cover and said absorbent body, said embossment region extending longitudinally along said intermediate portion of the article;

wherein the embossment region has a pattern-shape with back-and-forth cycles which traverse back-and-forth along the lateral direction;

the embossment region is continuous along each back-and-forth cycle of the pattern-shape; and the back-and-forth cycles of the embossment region are located proximate to and entirely inboard from the perimeter side-edges and end-edges of the absorbent body, the back-and-forth cycles of the embossment region thereby arranged to not intersect the perimeter edges of the absorbent body;

and wherein said embossment region extends continuously along at least about 1.5 back-and-forth cycles of the pattern-shape along at least said intermediate portion of the article.

2. An article as recited in claim 1, wherein said intermediate portion is a middle 34% of an overall, longitudinal length of the article.

3. An article as recited in claim 1, wherein said embossment region extends longitudinally at least 4 cm across said intermediate portion of the article.

4. An article as recited in claim 1, wherein said embossment region includes a pair of transversely spaced-apart, laterally opposed side-portions which extend generally along the longitudinal-direction at positions that are generally adjacent laterally opposed side-edges of the absorbent body, and a longitudinally opposed pair of end-portions which extend laterally along the cross-direction at positions that are generally adjacent a pair of longitudinally opposed end edges of the absorbent body.

5. An article as recited in claim 4, wherein said embossment region is located proximate a perimeter of the absorbent body, and extends along substantially an entirety of the perimeter of the absorbent body.

6. An article as recited in claim 1, wherein said embossment region has a traversing distance of at least about 0.1 cm, at least along said intermediate portion of the article.

7. An article as recited in claim 1, wherein said embossment region has a traversing distance of not more than about 2.3 cm, at least along said intermediate portion of the article.

8. An article as recited in claim 1, wherein said pattern-shape of said embossment region extends continuously with a traversing frequency of at least about 2 back-and-forth cycles per 5 cm of article length, at least along said intermediate portion of the article.

9. An article as recited in claim 1, wherein said embossment region has an overall, embossment region width of at least about 0.05 cm and not more than about 0.7 cm, as measured between an outboard edge of the embossment region and a corresponding, inboard edge of the embossment region.

10. An article as recited in claim 1, wherein said embossment region includes a first, longitudinally-extending, nonlinear embossment-element which is continuous along each back-and-forth cycle of the pattern-shape; and at least a second, longitudinally-extending, nonlinear embossment-element, which is continuous along each back-and-forth cycle of the pattern-shape and located proximately adjacent to said first embossment-element.

11. An article as recited in claim 10, wherein said embossment region includes a separation distance between the first and second embossment-elements which is at least about 0.05 cm and not more than about 0.8 cm.

12. An article as recited in claim 10, wherein said first embossment-element has a first embossment-element width, which is at least about 0.05 cm and not more than about 0.7 cm.

13. An article as recited in claim 12, wherein said second embossment-element has a second embossment-element width, which is at least about 0.05 cm and not more than about 0.7 cm.

14. An article as recited in claim 1, wherein said embossment region has an embossment caliper which is not more than about 37% of a central caliper of the article.

15. An article as recited in claim 1, wherein said embossment region is also formed into said cover and shaping layer along at least a portion of each end portion of the article.

* * * * *